(12) United States Patent
Sim

(10) Patent No.: US 9,090,697 B2
(45) Date of Patent: Jul. 28, 2015

(54) METHODS FOR TREATING BLEEDING DISORDERS

(71) Applicant: Bayer HealthCare LLC, Whippany, NJ (US)

(72) Inventor: Derek Sim, Burlingame, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 14/180,137

(22) Filed: Feb. 13, 2014

(65) Prior Publication Data

US 2014/0271625 A1 Sep. 18, 2014

Related U.S. Application Data

(60) Provisional application No. 61/786,672, filed on Mar. 15, 2013.

(51) Int. Cl.
*A61K 39/395* (2006.01)
*C07K 16/28* (2006.01)
*A61K 39/00* (2006.01)

(52) U.S. Cl.
CPC ....... *C07K 16/2896* (2013.01); *A61K 2039/505* (2013.01)

(58) Field of Classification Search
None
See application file for complete search history.

(56) References Cited

U.S. PATENT DOCUMENTS 5,693,762 A * 12/1997 Queen et al. ............... 530/387.3
2013/0108629 A1 * 5/2013 Dumont et al. ............ 424/134.1

OTHER PUBLICATIONS

Flocke et al., Eur J Cell Biol. Jun. 1992;58(1):62-70.*
Koszalka et al., Circ Res. Oct. 15, 2004;95(8):814-21. Epub Sep. 9, 2004.*
Stagg et al., Proc Natl Acad Sci U S A. Jan. 26, 2010;107(4):1547-52. doi: 10.1073/pnas.0908801107. Epub Jan. 4, 2010.*
Technical data sheet for Alexa Flour 488 Rat Anti-Mouse CD73, Bd Pharmingen, 561545 Rev. 1, 2011, 2 pages.*
Danckwardt et al., J Mol Med (Berl). Nov. 2013;91(11):1257-71. doi: 10.1007/s00109-013-1074-5. Epub Aug. 17, 2013.*
Magnus et al., Thromb Res. May 2014;133 Suppl 2:S1-9. doi: 10.1016/S0049-3848(14)50001-1.*
Gil-Bernabé et al., Br J Haematol. Aug. 2013;162(4):433-41. doi: 10.1111/bjh.12381. Epub May 21, 2013.*
Gómez-Outes et al., Vasc Health Risk Manag. 2013;9:207-28. doi: 10.2147/VHRM.S35843. Epub May 8, 2013.*
Koszalka et al., "Targeted Disruption of cd73/Ecto-5'-Nucleotidase Alters Thromboregulation and Augments Vascular Inflammatory Response", Journal of the American Heart Association, Circulation Research, 2004;95;814-821.

* cited by examiner

*Primary Examiner* — Michael Szperka
(74) *Attorney, Agent, or Firm* — Armstrong Teasdale LLP

(57) ABSTRACT

Disclosed are methods for treating bleeding disorders, such as hemophilia, in subjects in need thereof by administering an antibody that specifically binds CD73. The methods reduce production of adenosine, increase platelet activation and/or enhance the level of coagulation on the platelet surface to reduce and/or stop bleeding. In some embodiments, the methods can further include co-administering Factor VIII to treat the bleeding disorder.

15 Claims, 2 Drawing Sheets

METHODS FOR TREATING BLEEDING DISORDERS

This application claims priority to U.S. Provisional Patent Application No. 61/786,672, filed on Mar. 15, 2013, the disclosure of which is hereby expressly incorporated by reference in its entirety.

BACKGROUND OF THE DISCLOSURE

The present disclosure relates generally to methods for restoring hemostasis in bleeding disorders. More particularly, the present disclosure relates to a method for treating bleeding disorders, and in particular, hemophilia, by administering to a subject in need thereof an antibody that specifically binds CD73. In some embodiments, the methods further include administration of the combination of the antibody that specifically binds CD73 and Factor VIII.

Platelets (or thrombocytes) are small, irregularly shaped cell fragments derived from megakaryocytes that circulate in the blood of mammals and participate in hemostasis. In normal hemostasis, endothelial cells that line the inner surface of blood vessels prevent platelet activation by producing nitric oxide, endothelial-ADPase and PGI2. When the endothelial layer is injured, collagen, von Willebrand factor (vWF) and tissue factor from the subendothelium is exposed to the bloodstream. When the platelets contact collagen or vWF, they are activated, which is a critical component in the formation of a blood clot (thrombosis) to prevent blood loss. When hemostasis is hindered, however, thrombosis is slowed or even prevented, leading to severe loss of blood.

Conventionally, treatment efforts for abnormal hemostasis, such as found in subjects with bleeding disorders (e.g., hemophilia, von Willebrand Disease, etc.) or suffering severe trauma, have focused on the activation of the coagulation cascade system. The coagulation cascade system, shown in FIG. 1, involves two initial pathways, the extrinsic pathway and the intrinsic pathway. The extrinsic pathway involves tissue factor and Factor VII complex to activate Factor X, while the intrinsic pathway involves high-molecular weight kininogen, prekallikrein, and Factors XII, XI, IX and VIII to activate Factor X. Both the extrinsic and intrinsic pathways lead to a final common pathway in which Factor X mediates the generation of thrombin from prothrombin, with the ultimate production of fibrin from fibrinogen.

Platelets and endothelial cells also play important roles in hemostasis, and therefore, in bleeding disorders, it is now believed that normal hemostasis could potentially further be restored by modulating platelet and endothelial cell activities. More particularly, it is now believed that platelet activation and coagulation can be increased at the surface of endothelial cells, thereby generating a pro-hemostatic effect.

While treatments of bleeding disorders through the use of modulating/enhancing the coagulation cascade system have met with success, there exists a need to develop alternative mechanisms to restore hemostasis. Particularly, methods for activating platelets and increasing platelet surface coagulation at the site of endothelial cells themselves could prove advantageous in treating bleeding disorders. These methods alone, or in combination with conventional pro-coagulation cascade treatments, may provide for more efficient and effective generation of pro-hemostatic effects in subjects suffering from bleeding disorders and in other bleeding situations.

SUMMARY OF THE DISCLOSURE

The present disclosure generally relates to methods for treating bleeding disorders. More particularly, the present disclosure relates to methods for treating bleeding disorders, such as bleeding diseases including hemophilia, by administering an antibody that specifically binds CD73 to subjects in need thereof. It has been unexpectedly discovered that by targeting CD73, pro-hemostatic conditions can be effectively restored without solely targeting the coagulation cascade system. Inhibition of CD73 leads to less adenosine being generated, thereby increasing platelet activation and enhancing the level of coagulation on the platelet surface. In turn, bleeding time and total blood loss in the subject is reduced. In some embodiments, the methods can further include co-administering Factor VIII with the antibody that specifically binds CD73 to treat the bleeding disorder.

In one aspect, the present disclosure is directed to a method for treating a bleeding disorder in a subject in need thereof. The method comprises administering a therapeutically effective amount of an antibody or fragment thereof that specifically binds CD73.

In another aspect, the present disclosure is directed to a method for reducing bleeding time in a subject in need thereof. The method comprises administering a therapeutically effective amount of an antibody or fragment thereof that specifically binds CD73.

In another aspect, the present disclosure is directed to a method for treating hemophilia in a subject in need thereof. The method comprises administering a therapeutically effective amount of an antibody or fragment thereof that specifically binds CD73.

In yet another aspect, the present disclosure is directed to a method for reducing adenosine generation in a subject in need thereof. The method comprises administering a therapeutically effective amount of an antibody or fragment thereof that specifically binds CD73.

In another aspect, the present disclosure is directed to a method for increasing platelet activation in a subject in need thereof. The method comprises administering a therapeutically effective amount of an antibody or fragment thereof that specifically binds CD73.

In another aspect, the present disclosure is directed to a method for increasing platelet surface coagulation in a subject in need thereof. The method comprises administering a therapeutically effective amount of an antibody or fragment thereof that specifically binds CD73.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
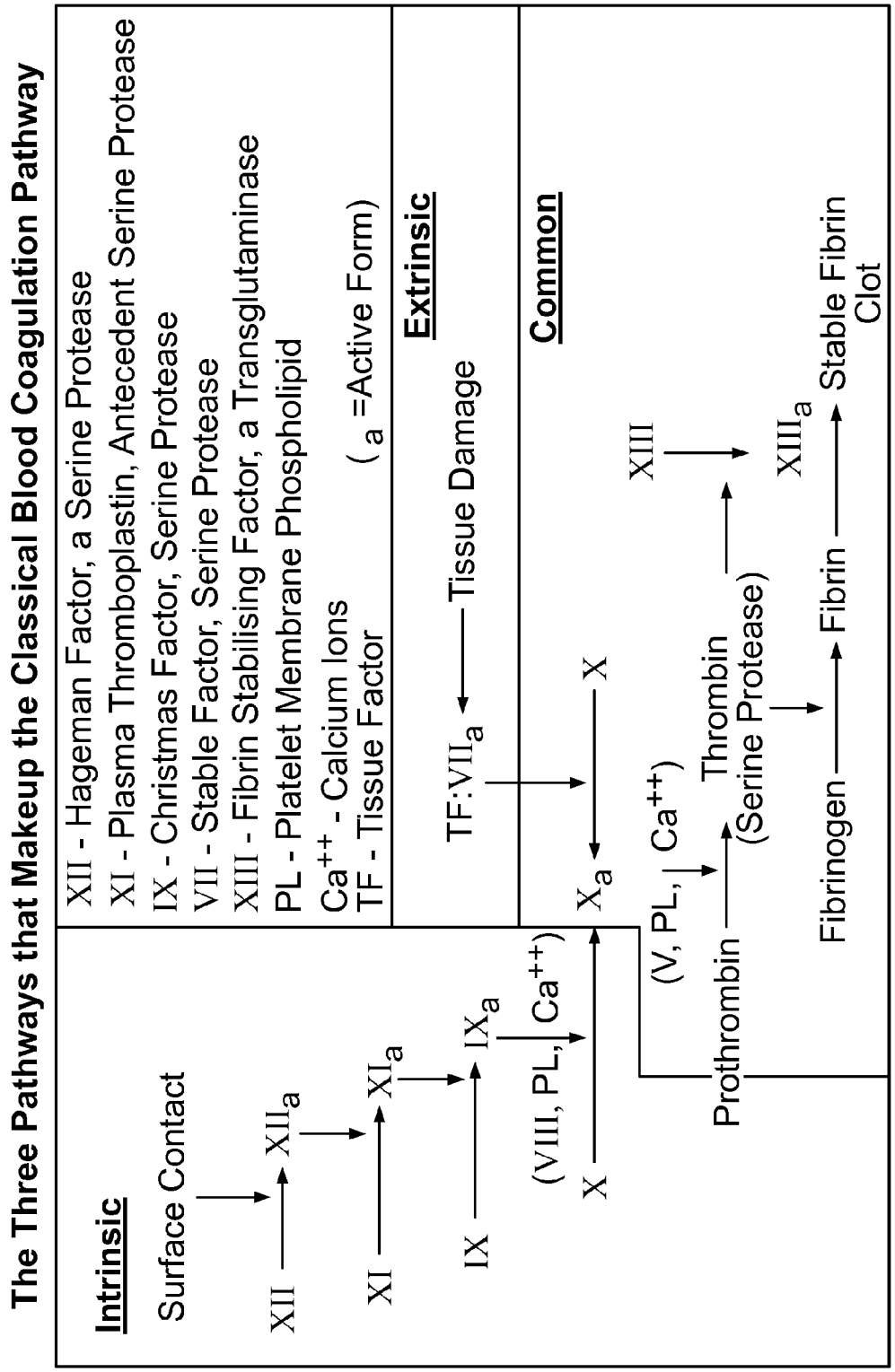
FIG. 1 is a schematic of the conventional coagulation cascade system.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

In accordance with the present disclosure, methods have been discovered that surprisingly allow for the treatment of bleeding disorders by targeting CD73 on the endothelium. Particularly, antibodies binding CD73 are administered to a subject in need thereof, and inhibit CD73 activation. This inhibition results in reduced production of adenosine and allows for increased levels of platelet activation and platelet surface coagulation to be achieved. The methods provide for reduced bleeding time and more efficient and effective generation of normal hemostasis in subjects in need thereof, and in particular, hemophiliacs.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein "bleeding disorder" refers to a disease or condition that impairs normal hemostasis. The bleeding disorder can be, for example, Hemophilia A, Hemophilia B, Factor VIII deficiency, Factor XI deficiency, von Willebrand Disease, Glanzmann's Thrombasthenia, Bernard Soulier Syndrome, idiopathic thrombocytopenic purpura, intracerebral hemorrhage, trauma, traumatic brain injury, and the like.

As used herein, "hemophilia" refers to a group of bleeding disorders associated with increased blood clot formation time as compared to blood clot formation time in healthy individuals without hemophilia. "Hemophilia" refers to both Hemophilia A, which is a disorder that leads to the production of defective Factor VIII, and Hemophilia B, which is a disorder that leads to the production of defective Factor IX.

As used herein, "trauma" refers to an injury resulting in sudden and severe blood loss. Exemplary traumas are known in the art and include, but are not limited to, intracerebral hemorrhage, traumatic brain injury, blunt trauma, penetrating trauma, and the like.

As used herein, "reducing bleeding time", "reduced bleeding time", and "reduction in bleeding time" refer to the shortening of the time period required for clot formation in a subject such to arrest bleeding, and thus provide a reduced bleeding volume, by administration of an antibody binding CD73 in comparison to a subject who does not receive the antibody.

As used herein, "pro-hemostatic condition" refers to the restoration of clot formation such to arrest bleeding. Further, "generation of a pro-hemostatic condition" refers to the restoration/generation of normal hemostasis in a subject by administration of an antibody binding CD73 in comparison to a subject who does not receive the antibody.

As used herein, "normal hemostasis" refers to the hemostasis process of a healthy subject not suffering from a bleeding disorder as defined herein.

As used herein, "susceptible" and "at risk" refer to having little resistance to a certain disease, disorder or condition, including being genetically predisposed, having a family history of, and/or having symptoms of the disease, disorder or condition.

As used herein, "human" antibody or antigen-binding fragment thereof refers to one that is not chimeric (e.g., not "humanized") and not from (either in whole or in part) a non-human species. A human antibody or antigen-binding fragment thereof can be derived from a human or can be a synthetic human antibody. A "synthetic human antibody" refers to an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or antigen-binding fragment thereof is one that is encoded by a nucleic acid isolated from a library of antibody sequences of human origin (e.g., such library being based on antibodies taken from a human natural source). Examples of human antibodies include antibodies as described in Soderlind et al., Nature Biotech. 2000, 18:853-856.

As used herein, "humanized antibody" or humanized antigen-binding fragment thereof refers to one that is (i) derived from a non-human source (e.g., a transgenic mouse which bears a heterologous immune system), which antibody is based on a human germline sequence; (ii) where amino acids of the framework regions of a non-human antibody are partially exchanged to human amino acid sequences by genetic engineering or (iii) CDR-grafted, wherein the CDRs of the variable domain are from a non-human origin, while one or more frameworks of the variable domain are of human origin and the constant domain (if any) is of human origin.

As used herein, "chimeric antibody" or antigen-binding fragment thereof refers to one, wherein the variable domains are derived from a non-human origin and some or all constant domains are derived from a human origin.

As used herein, "monoclonal antibody" refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to "polyclonal antibody" preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. The term monoclonal antibody specifically includes chimeric, humanized and human antibodies.

As used herein, an antibody "specifically binds", "binds specifically to", "is specific to/for" or "specifically recognizes" an antigen of interest, e.g., a polypeptide antigen target (here, CD73), is one that binds the antigen with sufficient affinity such that the antibody is useful as a therapeutic agent in targeting a cell or tissue expressing the antigen, and does not significantly cross-react with other proteins or does not significantly cross-react with proteins other than orthologs and variants (e.g., mutant forms, splice variants, or proteolytically truncated forms) of the aforementioned antigen target. The binding of the antibody to the antigen can be determined using methods known in the art, such as, for example surface plasmon resonance. The term "specifically recognizes" or "binds specifically to" or is "specific to/for" a particular polypeptide or an epitope on a particular polypeptide target as used herein can be exhibited, for example, by an antibody, or antigen-binding fragment thereof, having a monovalent $K_D$ for the antigen of less than $10^{-4}$ M, alternatively less than $10^{-5}$ M, alternatively less than $10^{-6}$ M, alternatively less than $10^{-7}$ M, alternatively less than $10^{-8}$ M, alternatively less than $10^{-9}$ M, alternatively less than $10^{-10}$ M, alternatively less than $10^{-11}$ M, alternatively less than $10^{-12}$ M, or less. An antibody "binds specifically to," is "specific to/for" or "specifically recognizes" an antigen if such antibody is able to discriminate between such antigen and one or more reference antigen(s).

In its most general form, "specific binding", "binds specifically to", is "specific to/for" or "specifically recognizes" is referring to the ability of the antibody to discriminate between the antigen of interest and an unrelated antigen, as determined, for example, in accordance with one of the following methods. Such methods can include, for example, Western blots, ELISA-, RIA-, ECL-, IRMA-tests and peptide scans. For example, a standard ELISA assay can be carried out. The scoring may be carried out by standard color development (e.g., secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 10 D. This means the difference between positive/negative is more than 5-fold, 10-fold, 50-fold, and preferably more than 100-fold. Typically, determination of binding specificity is performed by using not a single reference antigen, but a set of about three to five unrelated antigens, such as milk powder, BSA, transferrin or the like.

As used herein, "binding affinity" refers to the strength of the sum total of non-covalent interactions between a single binding site of a molecule and its binding partner. Unless indicated otherwise, as used herein, "binding affinity" refers to intrinsic binding affinity which reflects a 1:1 interaction between members of a binding pair (e.g., an antibody and an antigen). The dissociation constant "$K_D$" is commonly used to describe the affinity between a molecule (such as an antibody) and its binding partner (such as an antigen), i.e., how tightly a ligand binds to a particular protein. Ligand-protein affinities are influenced by non-covalent intermolecular interactions between the two molecules. Affinity can be measured by common methods known in the art, including for example plasmon surface resonance.

As used herein, "functional fragment" or "antigen-binding antibody fragment" of an antibody/immunoglobulin refer to a fragment of an antibody/immunoglobulin (e.g., a variable region of an IgG) that retains the antigen-binding region. An "antigen-binding region" of an antibody typically is found in one or more hypervariable region(s) of an antibody; however, the variable "framework" regions may also play an important role in antigen binding.

As used herein, "functional fragments" or "antigen-binding antibody fragments" refer to Fab, Fab', F(ab')$_2$, and Fv fragments; diabodies; single domain antibodies (DAbs), linear antibodies; single-chain antibody molecules (scFv); and multispecific, such as bi- and tri-specific, antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "multispecific" or "multi-functional" antibody is understood to have each of its binding sites identical. The F(ab')$_2$ or Fab may be engineered to minimize or completely remove the intermolecular disulphide interactions that occur between the $C_{H1}$ and $C_L$ domains.

All combinations of method or process steps as used herein can be performed in any order, unless otherwise specified or clearly implied to the contrary by the context in which the referenced combination is made.

Methods of Administering Antibodies Targeting CD73

The methods of the present disclosure generally include the administration of one or more antibodies that specifically bind CD73 (also referred to herein as "anti-CD73" antibodies) to a subject in need thereof. CD73 (ecto-5'-nucleotidase) is a 70 kDa glycosylphosphatidylinositol (GPI)-anchored cell surface molecule expressed on vascular endothelium. This protein is also found in certain populations of leukocytes, B cells, T cells, and in specific cells in lymphoid, bone marrow, thymic, kidney and liver tissues. CD73 catalyzes the extracellular conversion of 5'-AMP to adenosine. Adenosine binds to adenosine receptors to stimulate G-protein-coupled adenylyl cyclase in platelets to increase intracellular cAMP levels. cAMP activates protein kinase A (PKA), which phosphorylates several substrates to inhibit cytoskeletal reorganization, integrin activation and granule secretion and platelet aggregation. CD73 normally functions to prevent over-activation of platelets by converting extracellular 5'-AMP to adenosine.

The methods of the present disclosure administer anti-CD73 antibodies to promote/restore/maintain the hemostasis process during bleeding. Particularly, the methods of the present disclosure can prevent/control/reduce/treat bleeding disorders in subjects in need thereof; that is, by promoting/restoring/maintaining clot formation, the methods can prevent/reduce/control bleeding time, thereby preventing/controlling/reducing/treating bleeding disorders. As a further result, the methods of the present disclosure can control/reduce/minimize bleeding time, and also, control/reduce/minimize the amount of total blood loss when bleeding occurs.

Accordingly, by binding to and inhibiting the activity of CD73, the methods of the present disclosure can additionally reduce/prevent/control adenosine generation as compared to subjects that are not administered the anti-CD73 antibody. Further, by reducing adenosine generation, the methods of the present disclosure can increase/enhance/promote levels of platelet activation and increase/enhance/promote levels of coagulation on platelet surface as compared to subjects that are not administered the anti-CD73 antibody.

The anti-CD73 antibodies described below in detail and used in the methods of the present disclosure can be administered to a subset of subjects in need of promoting/restoring/maintaining the hemostasis process. Some subjects that are in specific need of restored/maintained hemostasis may include subjects who are susceptible to, or at elevated risk of, experiencing bleeding situations, including, but not limited to, subjects susceptible to, or at elevated risk of, bleeding disorders such as Hemophilia A, Hemophilia B, Factor VIII deficiency, Factor XI deficiency, von Willebrand Disease, Glanzmann's Thrombasthenia, Bernard Soulier Syndrome, idiopathic thrombocytopenic purpura, intracerebral hemorrhage, trauma, traumatic brain injury, and the like. In one particular embodiment, the methods can be administered to a subject who has, or is susceptible to, or at elevated risk of, hemophilia. Subjects may be susceptible to, or at elevated risk of, experiencing bleeding situations due to family history, age, environment, and/or lifestyle. Additionally, the methods can be administered to a subject to treat/control/reduce inflammation or for oncology purposes. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

Anti-CD73 antibodies can be administered alone in a suitable pharmaceutical formulation (i.e., no other active compound) or as a component of a suitable pharmaceutical formulation comprising the antibodies of interest in combination with another active compound such as Factor VIII, which is described more fully below. Additionally, the anti-CD73 antibodies, alone or in combination with another active compound such as Factor VIII, may be used in the manufacture of one or more medicaments. The pharmaceutical formulations may include one or more pharmaceutically acceptable carriers as are known in the art. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the formulation and not injurious to the subject. Lyophilized formulations, which may be reconstituted and administered, are also within the scope of the present disclosure.

Pharmaceutically acceptable carriers may be, for example, excipients, vehicles, diluents, and combinations thereof. For example, where the formulations are to be administered orally, they may be formulated as tablets, capsules, granules, powders, or syrups; or for parenteral administration, they may be formulated as injections (intramuscular, subcutaneous, intramedullary, intrathecal, intraventricular, intravenous), drop infusion preparations, or suppositories. For application by the ophthalmic mucous membrane route, they may be formulated as eye drops or eye ointments. These formulations can be prepared by conventional means, and, if desired, the active compound (i.e., anti-CD73 antibody or the anti-CD73 antibody in combination with Factor VIII) may be mixed with any conventional additive, such as an excipient, a binder, a disintegrating agent, a lubricant, a corrigent, a solubilizing agent, a suspension aid, an emulsifying agent, a coating agent, or combinations thereof.

Anti-CD73 Antibodies

Antibodies, and in particular, anti-CD73 antibodies, for administration in accordance with the methods of the present disclosure may be of many different forms. Suitable antibodies may be monoclonal and/or polyclonal antibodies, and may also be recombinant monoclonal and/or recombinant polyclonal antibodies. Both monoclonal and polyclonal antibodies of any type or subtype may be used such as, for example, IgM, IgG (IgG1, IgG2, etc.), IgA, IgD, and IgE. Other suitable antibodies include chimeric antibodies, bifunctional antibodies, bispecific antibodies, intact antibodies, antibody fragments, and combinations thereof. Suitable antibody fragments include antigen binding (variable) regions, antibody light chains, Fab, F(ab')$_2$, F(ab'), and combinations thereof. One particularly suitable anti-CD73 antibody for use in the methods of the present disclosure includes clone TY/23, available from BD PHARMINGEN, San Jose, Calif.

Antibodies may originate from human or any other species such as, for example, goat, rabbit, sheep, rat, mouse, chicken, donkey, and camel. Suitable antibodies may also be partially humanized through the chemical linking of human antibody components to other species' antibodies. Suitable antibodies may also be produced using recombinant protein expression methods.

Actual dosage levels of the anti-CD73 antibody in a pharmaceutical formulation for use in the methods of the present disclosure may be varied so as to obtain an amount of the antibody that is effective to achieve the desired therapeutic response or benefit for a particular subject, pharmaceutical formulation, and/or mode of administration. More particularly, as used herein, the phrase "therapeutically effective amount" of the anti-CD73 antibodies used in the methods of the present disclosure refers to a sufficient amount of the anti-CD73 antibodies to treat bleeding disorders as defined herein, at a reasonable benefit/risk ratio applicable to any medical treatment. It can be understood, however, that the total daily usage of the anti-CD73 antibodies and pharmaceutical formulations including the anti-CD73 antibodies for use in the methods of the present disclosure can be decided by the attending physician within the scope of sound medical judgment. The specific therapeutically effective dose level for any particular subject can depend upon a variety of factors including the bleeding disorder being treated and the severity of the bleeding disorder; activity of the specific anti-CD73 antibody employed; the specific pharmaceutical formulation employed; the age, body weight, general health, sex and diet of the subject; the time of administration, route of administration, and rate of excretion of the specific anti-CD73 antibody employed; the duration of the treatment; drugs used in combination or coincidental with the specific anti-CD73 antibody employed; and like factors well-known in the medical arts. For example, it is well within the skill of the art to start doses of the anti-CD73 antibodies at levels lower than required to achieve the desired therapeutic effect and to gradually increase the dosage until the desired therapeutic effect is achieved.

In some embodiments, the anti-CD73 antibodies can be administered to a subject in need thereof in an amount ranging from about 1.0 mg/kg total body weight of the subject to about 5.0 mg/kg total body weight of the subject per day and including from about 2.0 mg/kg total body weight to about 4.0 mg/kg total body weight of the subject per day. In one embodiment, the methods of the present disclosure include administering to a subject in need thereof about 2.0 mg/kg total body weight of the subject per day. In another embodiment, the methods of the present disclosure include administering to a subject in need thereof about 4.0 mg/kg total body weight of the subject per day. In some embodiments, the anti-CD73 antibodies can be administered to a subject in need thereof in daily amounts of from about 9.0 mg to about 565 mg, including from about 34 mg to about 340 mg, and including from about 45 mg to about 270 mg. Typically, the anti-CD73 antibodies may be administered to the subject daily for a period of from about 1 week to 1 month.

The daily dosage of anti-CD73 antibodies or pharmaceutical formulation including the anti-CD73 antibodies may be in the form of a single dosage or may be in the form of two dosages, three dosages, four dosages or more to be administered two or more times during the day.

Factor VIII

In some embodiments, the methods of the present disclosure include co-administering the anti-CD73 antibodies described above with a therapeutically effective amount of Factor VIII. Factor VIII, also known as anti-hemophilic factor (AHF), is a glycoprotein pro-cofactor produced in liver sinusoidal cells and endothelial cells outside of the liver throughout the body. This protein circulates in the bloodstream in an inactive form, bound to von Willebrand factor, until an injury that damages blood vessels occurs. In response to an injury, Factor VIII is activated and dissociates from von Willebrand factor. The active protein (sometimes written as Factor VIIIa) interacts with Factor IX in the coagulation cascade to activate Factor X. As noted above, Factor X then mediates the generation of thrombin from prothrombin, with the ultimate production of fibrin from fibrinogen to allow for clot formation.

In one embodiment, the methods include administering recombinant Factor VIII in combination with the anti-CD73 antibody. Recombinant Factor VIII refers to the production of Factor VIII by protein expression methods and chemical synthesis methods. Protein expression methods for producing recombinant proteins are known to those skilled in the art. Generally, "recombinant Factor VIII" is used herein to describe a Factor VIII polypeptide, which by virtue of its origin or manipulation, may not be associated with all or a portion of the polypeptide with which it is associated in nature and/or is linked to a polypeptide other than that to which it is linked in nature. Recombinant Factor VIII may not necessarily be translated from a designated nucleic acid sequence. For example, the recombinant Factor VIII can also be generated in any manner such as, for example, chemical synthesis methods including, for example, liquid-phase peptide synthesis, solid-phase peptide synthesis, fragment condensation, and chemical ligation.

One particularly suitable Factor VIII is commercially available as Kogenate FS (Bayer HealthCare Pharmaceuticals, Germany).

When co-administered with the anti-CD73 antibody, Factor VIII is administered in varying amounts such to be effective to achieve the desired therapeutic response for a particular subject, pharmaceutical formulation, and mode of administration. As used herein, the phrase "therapeutically effective amount" of Factor VIII used in the methods of the present disclosure refers to a sufficient amount of Factor VIII to be used in combination with the anti-CD73 antibody to improve the performance of the anti-CD73 antibody in treating bleeding disorders as defined herein, at a reasonable benefit/risk ratio applicable to any medical treatment. It can be understood, however, that the total daily usage of Factor VIII and pharmaceutical formulations including anti-CD73 antibody and Factor VIII for use in the methods of the present disclosure can be decided by the attending physician within the scope of sound medical judgment. The specific therapeutically effective dose level for any particular subject may depend upon a variety of factors including the bleeding disorder being treated and the severity of the bleeding disorder; the specific pharmaceutical formulation employed; the age, body weight, general health, sex and diet of the subject; the time of administration, and route of administration; the duration of the treatment; specific anti-CD73 antibody used in combination with Factor VIII; and like factors well-known in the medical arts. For example, it is well within the skill of the art to start doses of Factor VIII at levels lower than required to achieve the desired therapeutic effect and to gradually increase the dosage until the desired effect is achieved.

In some embodiments, Factor VIII can be co-administered with the anti-CD73 antibody in a subject in need thereof in a daily amount ranging from about 0.5 IU/kg total body weight of the subject to about 50 IU/kg total body weight of the subject.

The daily dosage of Factor VIII to be co-administered with the anti-CD73 antibodies may be in the form of a single dosage or may be in the form of two dosages, three dosages, four dosages or more to be administered two or more times during the day.

In an alternative embodiment, the anti-CD73 antibodies may be co-administered with one or more of Factor IX or XI. Factor IX is a zymogen (proenzyme) that is processed to remove the signal peptide, glycosylated and then cleaved by Factor IXa of the contact pathway or Factor VIIa of the tissue factor pathway to produce a two-chain form where the chains are linked by a disulfide bridge. When activated into Factor IXa, in the presence of $Ca^{2+}$, membrane phospholipids, and a Factor VIII cofactor, it hydrolyses one arginine-isoleucine bond in Factor X to form Factor Xa, which mediates the generation of thrombin from prothrombin as noted above. More particularly, Factor IX is a serine protease composed of four protein domains, a Gla domain, two tandem copies of the EGF domain, and a C-terminal trypsin-like peptidase domain, which carries out the catalytic cleavage. The N-terminal EGF domain has been shown to at least in part be responsible for binding tissue factor. Further, residues 88 to 109 of the second EGF domain mediate binding to platelets and assembly of the Factor X activating complex.

Factor XI (plasma thromboplastin antecedent) is the zymogen (proenzyme) form of Factor XIa. Factor XI circulates as a homodimer in an inactive form. Factor XI is activated into Factor XIa via cleavage by Factor XIIa, thrombin and autocatalysis. Active Factor XIa is a serine protease that activates Factor X to mediate the generation of thrombin from prothrombin as noted above.

In one embodiment, the methods include co-administering the anti-CD73 antibody with recombinant Factor IX, recombinant Factor XI and combinations thereof. Recombinant Factor IX and recombinant Factor XI refers to their production by protein expression methods and chemical synthesis methods. Protein expression methods for producing recombinant proteins are known to those skilled in the art. Generally, "recombinant Factor IX" and "recombinant Factor XI" used herein to describe Factor IX, and Factor XI polypeptides, which by virtue of their origin or manipulation, may not be associated with all or a portion of the polypeptide with which they are associated in nature and/or is linked to a polypeptide other than that to which they are linked in nature. Recombinant Factor IX and recombinant Factor XI may not necessarily be translated from a designated nucleic acid sequence. For example, the recombinant Factor IX and recombinant Factor XI can also be generated in any manner such as, for example, chemical synthesis methods including, for example, liquid-phase peptide synthesis, solid-phase peptide synthesis, fragment condensation, and chemical ligation.

Particularly suitable Factor IX sources are commercially available as Benefix® (Pfizer, New York, N.Y.) and Mononine® (CSL Behring, Sweden).

When co-administered with the anti-CD73 antibody, Factor IX and/or Factor XI can be administered in varying amounts such to be effective to achieve the desired therapeutic response for a particular subject, pharmaceutical formulation, and/or mode of administration. As used herein, the phrase "therapeutically effective amount" of Factor IX and/or Factor XI used in the methods of the present disclosure refers to a sufficient amount of Factor IX and/or Factor XI to be used in combination with the anti-CD73 antibodies to improve the performance of the anti-CD73 antibodies in treating bleeding disorders as defined herein, at a reasonable benefit/risk ratio applicable to any medical treatment. It can be understood, however, that the total daily usage of Factor IX and/or Factor XI and pharmaceutical formulations including anti-CD73 antibodies and Factor IX and/or Factor XI for use in the methods of the present disclosure can be decided by the attending physician within the scope of sound medical judgment. The specific therapeutically effective dose level for any particular subject may depend upon a variety of factors including the bleeding disorder being treated and the severity of the bleeding disorder; the specific pharmaceutical formulation employed; the age, body weight, general health, sex and diet of the subject; the time of administration, and route of administration; the duration of the treatment; specific anti-CD73 antibodies used in combination with Factor IX and/or Factor XI; and like factors well-known in the medical arts. For example, it is well within the skill of the art to start doses of Factor IX and/or Factor XI at levels lower than required to achieve the desired therapeutic effect and to gradually increase the dosage until the desired effect is achieved.

In some embodiments, Factor IX can be co-administered with the anti-CD73 antibodies in an amount ranging from about 0.5 IU/kg total body weight of the subject to about 50 IU/kg total body weight of the subject per day.

The daily dosage of Factor IX and/or Factor XI to be co-administered with the anti-CD73 antibodies may be in the form of a single dosage or may be in the form of two dosages, three dosages, four dosages or more to be administered two or more times during the day.

The disclosure will be more fully understood upon consideration of the following Example, which is given solely for the purpose of illustration and is not to be construed as limiting of the present disclosure, as many variations thereof are possible without departing from the spirit and scope of the disclosure.

EXAMPLE

In this Example, the effect of administering anti-CD73 monoclonal antibodies on reduction in blood loss in mice with Hemophilia A mice was analyzed.

Male Hemophilia A mice, approximately eight to nine weeks of age and weighing, on average, approximately 25 grams, were used in this Example. The mice were anesthetized with isoflurane and the tails were placed in approximately 37-38° C. warmed 15-ml plastic tubes including 0.9% (by weight) saline for 10 minutes. The tails were then cut at 4 mm from the tip by scalpel and immediately placed back into separate pre-warmed (37-38° C.) 15-ml plastic tubes containing 10 ml of 0.9% (by weight) saline. Each mouse was allowed to bleed freely for 40 minutes.

Twenty-four hours prior to the tail cut, each mouse having Hemophilia A was injected, via tail injection, with one of the following: 4 mg/kg (100 μg) isotype antibody (9 mice), 4 mg/kg (100 μg) of anti-CD73 monoclonal antibody (clone TY/23, BD PHARMINGEN, San Jose, Calif.) (16 mice), 20 IU/kg (0.5 IU) of Factor VIII (commercially available as Kogenate FS (Bayer HealthCare Pharmaceuticals, Germany)) (17 mice), a pharmaceutical formulation including 4 mg/kg (100 μg) isotype antibody and 20 IU/kg (0.5 IU) of Factor VIII (9 mice), a pharmaceutical formulation including 2 mg/kg (50 μg) of anti-CD73 monoclonal antibody and 20 IU/kg (0.5 IU) of Factor VIII (17 mice), or a pharmaceutical formulation including 4 mg/kg (100 μg) of anti-CD73 antibody and 20 IU/kg (0.5 IU) of Factor VIII (17 mice). Eighteen mice were left completely untreated prior to the tail cut to serve as an untreated control.

Blood loss was quantified gravimetrically by weighing the tubes before and after blood was collected. The results are shown in FIG. 2.

Figure 2:
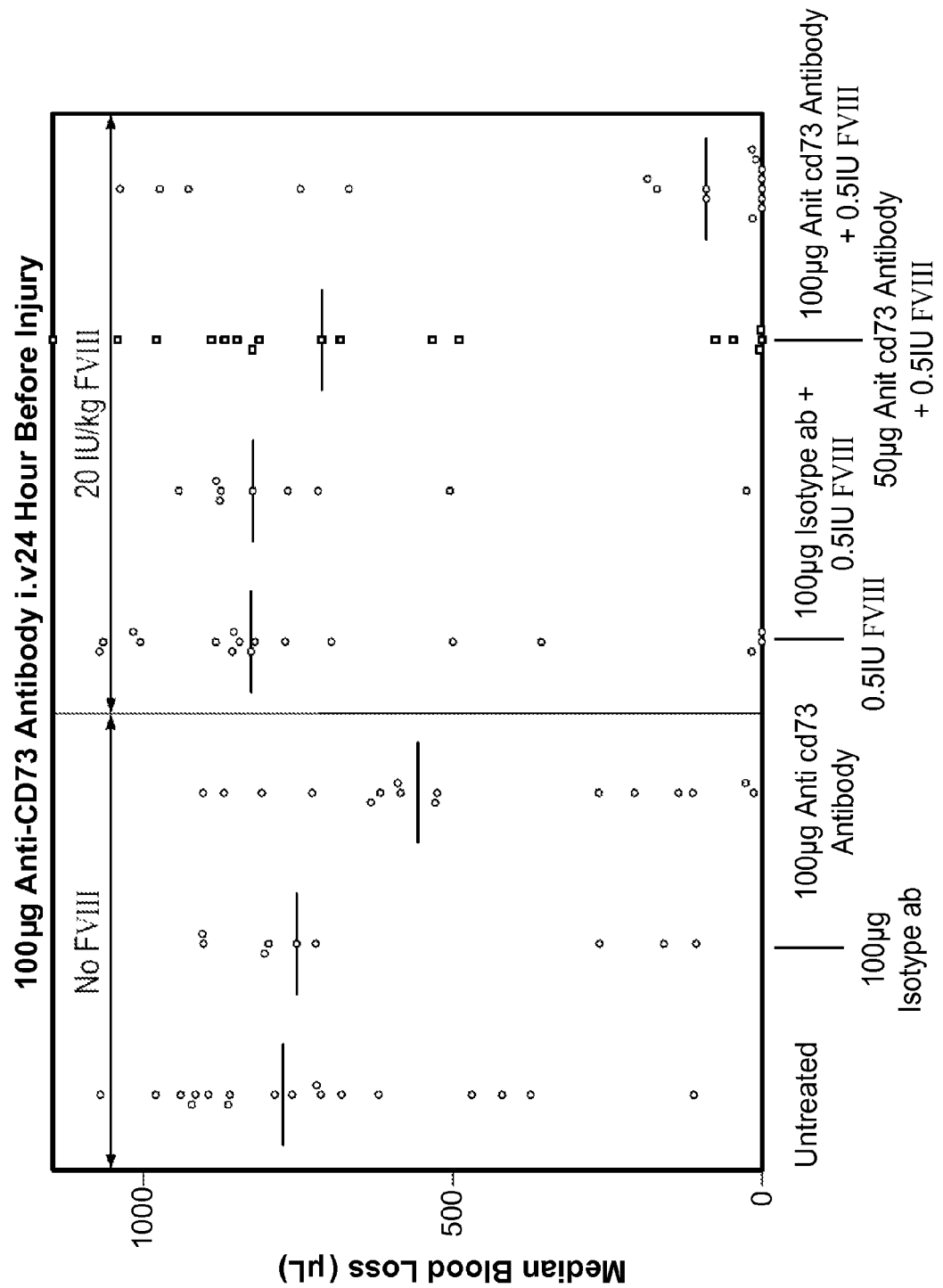
FIG. 2 is a graph depicting the effect of anti-CD73 monoclonal antibody on median blood loss as analyzed in Example 1.

As shown in FIG. 2, inhibition of CD73 by anti-CD73 antibodies reduced blood loss in mice having Hemophilia A. A dose dependent effect was also observed when the anti-CD73 antibody was used in combination with administration of Factor VIII. These results demonstrate that inhibition of targets unrelated to the coagulation cascade, such as CD73, can provide for pro-hemostatic effects.

What is claimed is:

1. A method for treating a bleeding disorder in a subject in need thereof, the method comprising administering a therapeutically effective amount of an antibody or fragment thereof that specifically binds CD73 and inhibits CD73 activity.

2. The method of claim 1 wherein the antibody is a monoclonal antibody.

3. The method of claim 1 wherein the antibody is a recombinant monoclonal antibody.

4. The method of claim 1 wherein the antibody is a humanized antibody.

5. The method of claim 1 further comprising co-administering a therapeutically effective amount of Factor VIII.

6. The method of claim 5 wherein the Factor VIII is a recombinant Factor VIII.

7. The method of claim 1 wherein the bleeding disorder is selected from the group consisting of Hemophilia A, Hemophilia B, Factor VIII deficiency, Factor XI deficiency, von Willebrand Disease, Glanzmann's Thrombasthenia, Bernard Soulier Syndrome, idiopathic thrombocytopenic purpura, and trauma.

8. The method of claim 1 wherein the antibody or fragment thereof is administered to the subject in need thereof in an amount of from about 9.0 milligrams to about 565 milligrams per day.

9. The method of claim 1 wherein the treating includes reducing bleeding time in the subject in need thereof.

10. The method of claim 1 wherein the bleeding disorder is hemophilia.

11. A method for increasing platelet activation in a subject in need thereof, the method comprising administering a therapeutically effective amount of an antibody or fragment thereof that specifically binds CD73 and inhibits CD73 activity.

12. The method of claim 11 wherein the antibody is a monoclonal antibody.

13. The method of claim 11 wherein the antibody is a humanized antibody.

14. The method of claim 11 wherein the antibody is a recombinant monoclonal antibody.

15. The method of claim 11 wherein the antibody or fragment thereof is administered to the subject in need thereof in an amount of from about 9.0 milligrams to about 565 milligrams per day.

* * * * *